United States Patent [19]

Fraleigh

[11] Patent Number: 4,539,838

[45] Date of Patent: Sep. 10, 1985

[54] VARIABLE VOLUME DUAL ACTION RHEOMETER

[76] Inventor: M. Foster Fraleigh, 4524 Hudson Dr., Stow, Ohio 44224

[21] Appl. No.: 544,442

[22] Filed: Oct. 21, 1983

[51] Int. Cl.³ .............................................. G01N 11/14
[52] U.S. Cl. .......................................... 73/59; 73/841; 374/48
[58] Field of Search ....................... 73/59, 841; 374/48, 374/47

[56] References Cited

U.S. PATENT DOCUMENTS 3,182,494  5/1965  Beatty et al. ........................... 374/48
4,337,646  7/1982  Fraleigh ................................... 73/59

Primary Examiner—Jerry W. Myracle
Assistant Examiner—Joseph W. Roskos
Attorney, Agent, or Firm—Oldham, Oldham & Weber Co.

[57] ABSTRACT

The invention comprises a device which performs the functions of both a Mooney Viscometer and an Oscillating Disk Rheometer to measure the visco-elastic properties of rubber and rubber-like materials. Rotational and oscillating motion are transmitted to a shaft by means of a sprocket and a hub connected to an eccentric. Rubber samples having a wide range of stiffnesses can be accommodated by a provision for changing the thickness of the sample.

6 Claims, 2 Drawing Figures

VARIABLE VOLUME DUAL ACTION RHEOMETER

TECHNICAL FIELD

This invention lies primarily in the art of physical testing devices for rubber and rubber-like substances. More particularly, the invention is directed to a measurement device which can perform two distinct types of tests commonly employed in characterizing the curing properties of the rubber. The need for separate machines to perform each test is thus eliminated.

BACKGROUND ART

A multitude of testing methods have heretofore been available for measuring the curing characteristics of elastomeric materials. These devices generally measure to change in visco-elastic properties of the material as the cure proceeds, that is, they measure how the cross-linking of the molecular chains alters viscosity and elastic properties. Two of the most widely accepted and useful devices for measuring cure rate are the Mooney Viscometer and the Monsanto Oscillating Disk Rheometer.

The Mooney device measures shear viscosity, utilitizing a disc which rotates in a shallow cavity to produce a shearing action. The disc contains a number of serrated edges which aid in gripping the rubber. Uncured rubber placed in the cavity is heated to curing temperature. The increase in viscosity caused by the crosslinking during the cure is reflected in a measurably increased resistance to rotation of the disc. As the cure proceeds further, the integrity of the rubber sample is lost because the increased elasticity results in tearing of the sample where it contacts the rotating disc.

The Oscillating Disk Rheometer, on the other hand, is capable of measuring the complete curing characteristics of a rubber sample. As the name implies, a disc embedded in the sample oscillates rather than rotates to produce a shear strain in the rubber. The torque needed to produce the oscillation is proportional to the shear modulus or stiffness of the material which naturally increases during cure. A torque transducer relates the measured torque to a signal which is than plotted on a "rheograph".

Both these devices have certain drawbacks, not the least being their high initial cost and maintenance. The rubber samples tend to adhere to the disc, making turnaround time on either device high because all material from a previous test must be removed prior to subsequent testing. With the oscillating disc, provisions must be made for varying the amplitude of the oscillations so that torque requirements remain within acceptable limits regardless of sample stiffness.

U.S Pat. No. 4,337,646 to the instant inventor, addresses the problem of rubber adhering to the disc but does not discuss what will hereinafter be disclosed, namely, a device for combining the functions of a Mooney Viscometer and an oscillating disc in one device, and an improved design for torque adjustment which does not involve amplitude variation.

DISCLOSURE OF INVENTION

Accordingly an aspect of the invention is to provide a device for measuring a plurality of elastomeric properties.

Another aspect of the invention is to provide a device, as above, which can replace both a Mooney Viscometer and an oscillating disc rheometer.

Yet another aspect of the invention is to provide a device, as above, having a measurement cavitity whose volume can be varied to accommodate elastomers of various stiffnesses.

Still another aspect of the invention is to provide a device, as above, which can be quickly and easily manipulated to perform the desired test.

These aspects, and others which will be disclosed hereinafter, are achieved by a multi-mode elastomeric testing device, comprising: a measurement cavity formed at the junction of an upper and a lower platen; a rotor disposed in said cavity, having sealment means to said cavity and including a head and shank portion; a shaft in mechanical engagement with said shank; means for transmitting oscillatory motion to said shaft, including a hub positioned on said shaft and detachably linked to an eccentric via a rod; means for transmitting rotational motion to said shaft, including a first sprocket positioned on said shaft and mechanically linked to a second sprocket via a belt; and a power source connected to both said transmission means and including a torque transducer; wherein said hub is keyed to said shaft and said sprocket is received by said hub and rotates freely thereon.

BRIEF DESCRIPTION OF DRAWINGS

For a fuller understanding of the invention, the following detailed description should be read in conjunction with the drawings, wherein.

BEST MODE FOR CARRYING OUT THE INVENTION

Figure 1:
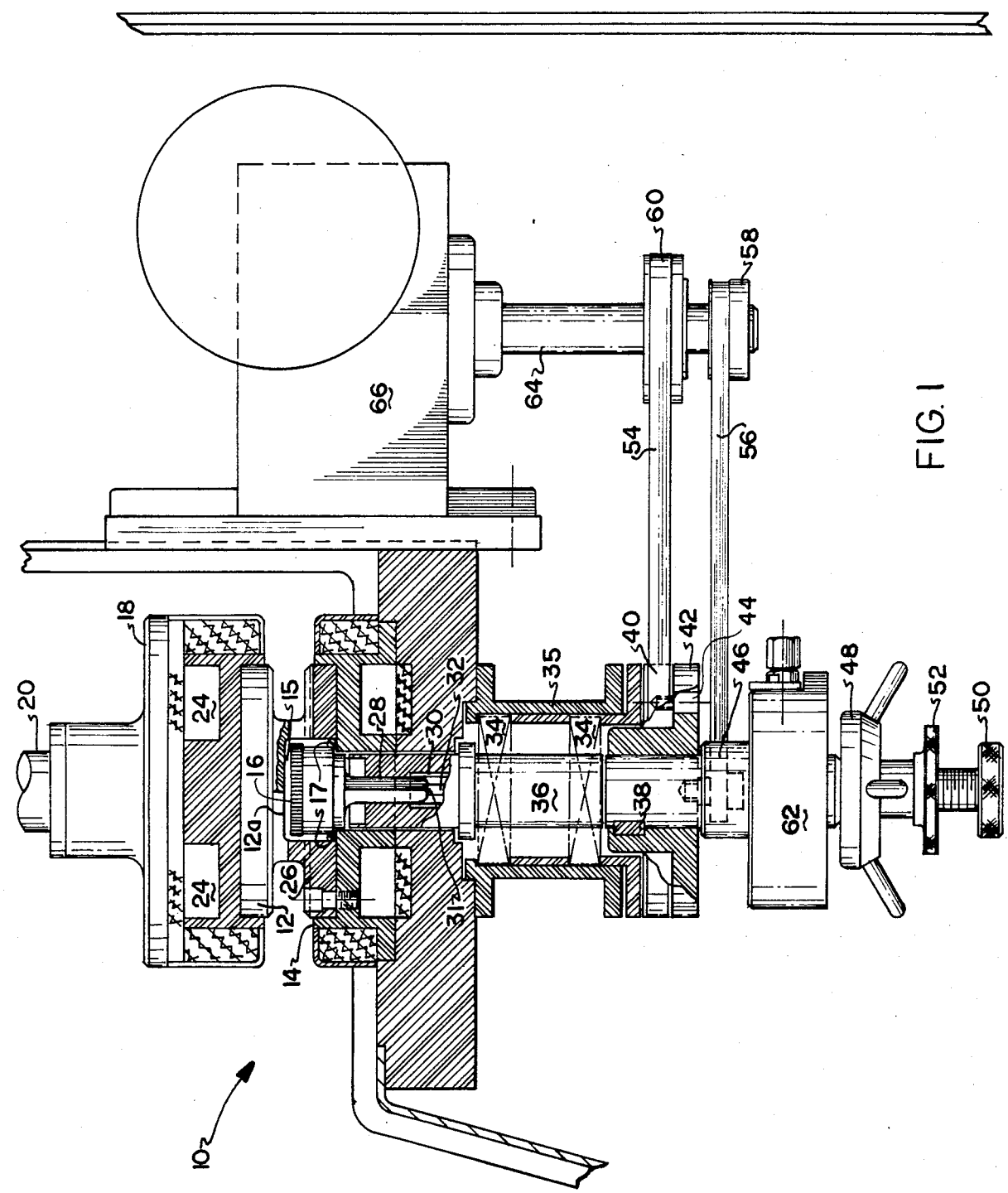
FIG. 1 is a front elevation cross-sectional view of the invention.
Figure 2:
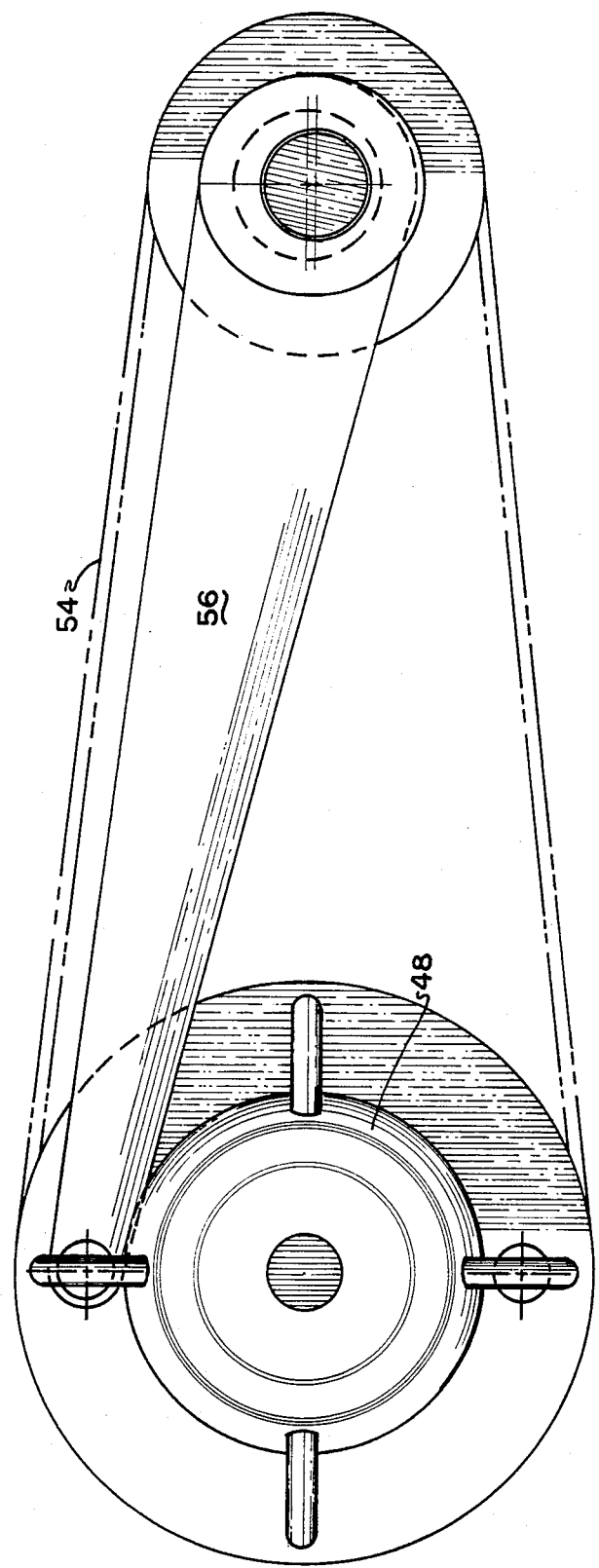
FIG. 2 is a top sectional view showing interconnection of the device to a drive system.

FIG. 1 illustrates in detail the structure of the invention, wherein a variable volume dual action rheometer is indicated generally by the number 10. Upper and lower platens 12 and 14 respectively define a measurement cavity 15 having disposed therein a rotor 16 which directly contacts the rubber sample during the test procedure. The preferred design for the rotor, lower platen and sealment means between the two is contained in U.S. Pat. No. 4,337,646 to the instant inventor and which is hereby incorporated by reference. In brief terms, this issued patent discloses a rotor head similar to that of the instant FIG. 1 having an elastomeric seal 17 located in a die ring 26.

The upper platen 12 can be raised, as is conventional in the art. The platen preferably has a heating means, such as heater cartridges 24 contained in a heater housing 22. An adaptor plate 18 joins the heater housing to a hydraulic or air piston which in turn can be raised or lowered by the operator.

Returning to the rotor, a shank portion 28 extends downward within a shaft 36 and is received by a chuck or collet 30 which can be spring loaded to facilitate removal of the rotor when required. The shank tip 31 abuts against an adjustment pin 32 which runs concentrically through the collet and which functions to position the rotor within the cavity 15. The height of the adjustment pin is controlled by the adjustment screw 50 which connects to the pin 32 by well known means and includes a locking nut 52 to maintain a predetermined setting. Similarly, rotor locking wheel 48 provides for a tight engagement between the collet 30 and the rotor shank.

As mentioned previously, there are two basic tests used to measure visco-elastic properties in rubber like materials. For Mooney Viscosity measurements, a rotational movement must be imparted to the rotor. In contrast, for the oscillating disc measurement, the rotor must move in oscillatory fashion having an amplitude of only a few degrees of arc. Both of these types of motion can be provided by the instant invention, which includes a sprocket 40 and a hub 42. Connected to the hub in removable fashion is a rod 56 which in turn is connected to an eccentric 58. The sprocket 40 is connected to a second sprocket 60 via a timing chain or belt 54. Sprocket 60 and the eccentric 58 are keyed to a motor shaft 64 which is a source of rotational movement.

While the hub 42 is secured to the shaft through a key 38 or other means, the sprocket 40 is free to rotate about the outer perimeter of the hub. If it is desired to provide a Mooney test of a rubber sample, the rotational motion of the sprocket 40 is transmitted through the hub and into the shaft 36 by means of a hub pin 44 which, as shown, passes both through the hub and an aperture in the sprocket 40. Conversely, when an oscillatory motion is desired, the hub pin 44 is removed so that the sprocket now spins freely. The rod 56 is then attached at a radial position on the hub by means of an oscillator arm pin 46, thereby transferring to the hub the oscillating motion created by movement of the rod about the eccentric 58. Naturally, at no time should both the hub pin 44 and the oscillator arm pin 46 be connected.

In addition to the above elements, those skilled in the art will appreciate that the invention includes various conventional components such as bearings 34 which allow free rotation of shaft 36 and which are contained in a bearing housing 35. The motor used to drive the shaft 64 is most preferably electric and utilizes a gear reduction 66. A torque transducer of conventional design is also used to translate the torque needed to rotate or oscillate the shaft into an electrical, mechanical, or pneumatic signal which is then displayed in graphic form. Preferably, the torque transducer is positioned coaxially with the shaft, but may alternatively be located on the motor shaft 64.

The advantages of the invention over the prior art are two-fold. First, by combining the functions of both the Mooney viscometer and the oscillating disk rheometer into one device, considerable cost savings are realized. The combining of these functions has heretofore been thought unfeasible because of the disparity in structure of the standard prior art devices. That is, the Mooney and oscillating disk tests, as defined by ASTM standards, have widely different requirements for cavity size, disc shape, and heat history. It has unexpectedly been found however, that the device of the invention can duplicate closely and consistently the results obtainable using separate machines.

The second advantage of the invention refers specifically to its use in the oscillating disk mode. In both the instant invention and in the prior art, it is necessary to keep the measured torque within a certain value range for reasons of equipment protection and measurement accuracy. As mentioned in the background, prior art devices maintain torque limits by controlling the amplitude of the oscillations, which is both complicated and expensive. The instant invention, on the other hand, limits torque by sample thickness. This is illustrated in the following procedure.

A rubber sample placed in cavity 15 contacts the upper surface 16A of the rotor which contains a plurality of grooves to provide frictional adhesion. The shear strain on the sample for any given amplitude of oscillation is a function of the sample thickness, that is, the distance between upper surface 16A of the rotor and inner surface 12A of the upper platen 12. If the rubber sample is too stiff and therefore requires a torque value for oscillation beyond a desired range, the rotor is lowered via the adjustment pin 30 and the adjustment screw 50. Because the thickness of the sample must be known to a high degree of accuracy, discs having a known thickness can be placed on the upper surface of the rotor and the adjustment pin lowered until the disc contacts the platen surface 12A. The upper platen is then raised, the disc or discs removed and the rubber sample inserted for measurement. A similar procedure is used if the rubber to be measured has a low amount of stiffness. In this case, the rotor is raised so that the thickness of the rubber sample is decreased. By varying the thickness of the sample, the need for providing different settings of oscillation amplitude is eliminated.

The above disclosure represents the best mode and the preferred embodiments of the invention as required by the patent statutes. It will be appreciated, however, that modifications can be made thereto without departing from the scope as defined by the following attached claims.

What is claimed is:

1. A multi-mode elastomeric testing device, comprising:
   a measurement cavity formed at the junction of an upper and a lower platen;
   a rotor disposed in said cavity, having sealment means to said cavity and including a head and shank portion;
   a shaft in mechanical engagement with said shank;
   means for transmitting oscillatory motion to said shaft, including a hub positioned on said shaft and detachably linked to an eccentric via a rod;
   means for transmitting rotational motion to said shaft, including a first sprocket positioned on said shaft and mechanically linked to a second sprocket via a belt; and
   a power source connected to both said transmission means and including a torque transducer;
   wherein said hub is keyed to said shaft and said sprocket is received by said hub and rotates freely thereon.

2. A testing device according to claim 1, wherein said transducer is positioned on said shaft and wherein said testing device includes an adjustment pin for raising and lowering said rotor, said adjustment pin being positioned via an adjustment screw concentrically disposed within said shaft.

3. A testing device according to claim 2, wherein said shank portion is releasably secured by a collet, said hub is detachably linked to said rod by a pin and wherein said hub and said first sprocket are detachably linked by a pin.

4. A multi-mode elastomeric testing device, comprising:
   a measurement cavity formed at the junction of an upper and a lower platen;

a rotor disposed in said cavity, having sealment means to said cavity and including a head and shank portion;

a shaft in mechanical engagement with said shank;

means for transmitting oscillatory motion to said shaft;

means for transmitting rotational motion to said shaft; and a power source connected to both said transmission means and including a torque transducer.

5. A testing device according to claim 4 wherein said means for transmitting rotational motion to said shaft includes a first sprocket positioned on said shaft and mechanically linked to a second sprocket via a belt.

6. A testing device according to claim 5 wherein said means for transmitting oscillatory motion to said shaft includes a hub positioned on said shaft and detachably linked to an eccentric via a rod.

* * * * *